United States Patent [19]

Buchanan

[11] 4,198,427

[45] Apr. 15, 1980

[54] INSECTICIDAL CARBAMATES

[75] Inventor: James B. Buchanan, Wilmington, Del.

[73] Assignee: E. I. Du Pont de Nemours and Company, Wilmington, Del.

[21] Appl. No.: 920,838

[22] Filed: Jun. 30, 1978

Related U.S. Application Data

[63] Continuation-in-part of Ser. No. 791,255, Apr. 27, 1977, abandoned.

[30] Foreign Application Priority Data

Sep. 10, 1977 [JP] Japan .................. 77/121920[U]
Jan. 30, 1978 [JP] Japan .................. 78/9012[U]

[51] Int. Cl.$^2$ ............... C07C 119/18; A01N 9/12
[52] U.S. Cl. ........................... 424/298; 260/453 RW
[58] Field of Search ............... 260/453 RW; 424/298

[56] References Cited

U.S. PATENT DOCUMENTS

| | | | |
|---|---|---|---|
| 3,506,698 | 4/1970 | Jelinek | 260/453 RW |
| 3,514,516 | 5/1970 | Summers | 260/453 RW |
| 3,576,834 | 4/1971 | Buchanan | 260/453 R |
| 3,632,621 | 1/1972 | Addor et al. | 260/453 RW |
| 3,752,841 | 8/1973 | Fuchs | 260/453 RW |
| 3,939,192 | 2/1976 | Kuhle et al. | 260/453 R |

OTHER PUBLICATIONS

Chem. Abstracts, 79, 74964v.
Chem. Abstracts, 82, 120118j.
Federal Register, 27, 2267–2277 (Mar. 9, 1962).

*Primary Examiner*—Alan L. Rotman
*Assistant Examiner*—Robert C. Whittenbaugh

[57] ABSTRACT

A composition useful as an insecticide containing a reation product of formaldehyde and a compound such as methomyl.

26 Claims, No Drawings

INSECTICIDAL CARBAMATES

RELATED APPLICATION

This is a continuation-in-part of copending application Ser. No. 791,255 filed Apr. 27, 1977, and now abandoned.

BACKGROUND OF THE INVENTION

This invention relates to insecticidal carbamates.

U.S. Pat. No. 3,576,834, assigned to Du Pont, discloses insecticides such as methomyl which has the structure

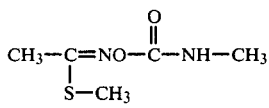

SUMMARY OF THE INVENTION

This invention relates to insecticidal compositions containing a reaction product of formaldehyde and a compound of formula I and to the method of use of these compositions.

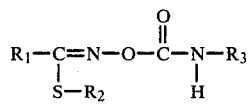

where
- $R_1$ is a branched or straight chain alkyl of 1–3 carbon atoms;
- $R_2$ is a branched or straight chain alkyl of 1–3 carbon atoms; and
- $R_3$ is methyl or hydrogen.

Also this invention relates to a compound of formula II, which is formed by reacting formaldehyde with a compound of formula I.

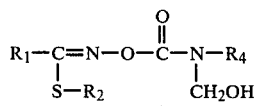

where
- $R_1$ and $R_2$ are as defined and
- $R_4$ is methyl, hydrogen or $CH_2OH$.

DETAILED DESCRIPTION OF THE INVENTION

Preferred Embodiments

Compositions which are preferred due to their insecticidal activity are those which contain a reaction product of formaldehyde and a compound of formula I where $R_1$, $R_2$ and $R_3$ are $CH_3$, namely N-[N-(methylamino)carbonyloxy]ethanimidothioic acid, methyl ester.

Preferred compounds of formula II are where
- $R_1$ is methyl or ethyl;
- $R_2$ is methyl or ethyl; and
- $R_4$ is hydrogen or methyl.

A preferred compound of formula II is N-[N-(hydroxymethyl)-N-methylaminocarbonyloxy]ethanimidothioic acid, methyl ester.

Preparation

Compositions of this invention can be prepared by reacting a substituted N-(aminocarbonyloxy)alkanimidothioic acid ester of formula I with formaldehyde, preferably in the presence of a base.

If $R_3$ is methyl, the process is represented by Equation I.

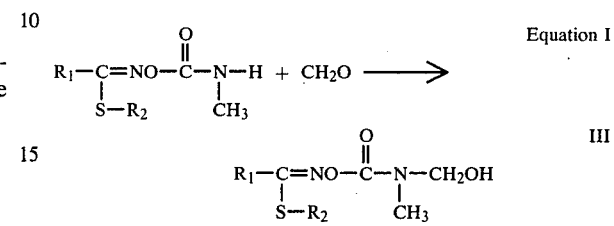

Although Equation I is represented as resulting in a simple reaction compound, it is to be understood that other constituents will be present. However, the compound of formula III (where $R_3$ is methyl) is present in a substantial amount in the reaction product.

As employed herein, "reaction product" includes all of the compounds formed in a reaction of formaldehyde and a compound of formula I. The term "reaction product" excludes unreacted compound of formula I and formaldehyde.

As illustrative of an additional reaction product, under the same conditions formaldehyde may react with the initial product (III) to form further condensation products represented by formula IV.

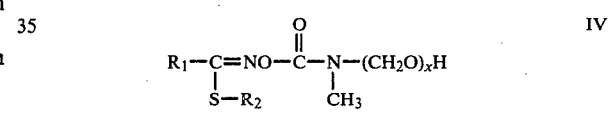

where
$x = 2, 3, 4$ (higher integers may also be present).

If formed, these products will be present in the composition.

If $R_3$ is hydrogen, the process is represented by Equation II, and a mixture of compounds, comprised chiefly of the monomethylol (V) and dimethylol (VI) derivatives is formed.

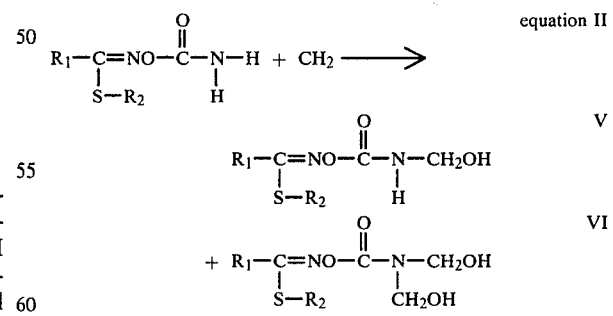

Although the reaction compounds of formula V and VI will be present in a substantial amount, the reaction product, in addition, will contain other compounds formed in the reaction. Further condensation of formaldehyde with the hydroxyl functions of the compounds of formulae V and VI can take place under some conditions.

Usually a small proportion of the starting material of formula I does not react with formaldehyde. This unreacted material will be present in the composition. Also, unreacted formaldehyde can be present.

Preparation of the compounds of formula I used as starting materials is described in U.S. Pat. Nos. 3,574,736; 3,576,834 and 3,787,470. Suitable sources of formaldehyde are a commercial 37% by weight aqueous solution stabilized with methanol and a mixture of polyoxymethylene glycols known as paraformaldehyde. Trioxane, the cyclic trimer of formaldehyde, may also be used. Information on the chemistry of formaldehyde is available in "Formaldehyde," by J. F. Walker, 2nd Edn., Reinhold Publishing Co., New York, 1953. Any source of formaldehyde can be used in making the reaction product.

The molar ratio of compound of formula I to formaldehyde can vary from 1:0.1 to 1:50. More preferred is a molar ratio of 1:0.5 to 1:5. It is most preferred to use a ratio of the compound of formula I to formaldehyde in the range of 1:1 to 1:3.

The reaction is generally carried out in a suitable solvent such as water, methanol, ethanol, dioxane or tetrahydrofuran. Mixtures of solvents can also be used. Bases suitable for the process of this invention include bicarbonate, carbonates and hydroxides of alkali metals and alkaline earths, and organic bases, such as trimethylamine, triethylamine, pyridine and N,N-dimethylaniline. It is also possible to carry out the process in the absence of a base, but generally it is inconveniently slow and incomplete.

The process is carried out at temperatures of between about 0° and 100° C., preferably between 20° and 60° C. The process may be run at atmospheric pressure or in a closed system under autogenous pressure.

In the examples of this disclosure, parts are by weight, and temperatures are in degrees centigrade unless otherwise indicated.

EXAMPLE 1

A.

A mixture of 16.0 parts of N-[N-methylaminocarbonyloxy]ethanimidothioic acid, methyl ester, 6.0 parts of paraformaldehyde, 1.0 part of sodium bicarbonate and 53.0 parts of water is stirred at ambient temperature (about 25°). At first, the mixture contains suspended solids, but after a few hours of stirring a clear solution results. Stirring is continued for a total of about 40 hours. To the solution is added dilute sulfuric acid until the pH is 6.5; the final weight of the solution amounts to 82.0 parts.

Examination of this solution by thin layer chromatography indicates that the N-[N-methylaminocarbonyloxy]ethanimidothioic acid, methyl ester, starting material has been largely converted to the methylol derivative.

B.

A mixture of 32.4 parts of N-[N-methylaminocarbonyloxy]ethanimidothioic acid, methyl ester, 3.0 parts of paraformaldehyde and 65 parts of water is stirred at 75°–80° for four hours. Water is added, causing a considerable amount of N-[N-methylaminocarbonyloxy]ethanimidothioic acid, methyl ester to crystallize out. This is filtered off. The filtrate (about 150 parts) is extracted three times with methylene chloride, each time with about 200 parts; these extracts contain mostly unreacted N-[N-methylaminocarbonyloxy]ethanimidothioic acid, methyl ester. The aqueous phase is then extracted a further three times with methylene chloride, each time with about 135 parts. Evaporation of the solvent from these extracts yields a small amount of an oil. The NMR spectrum of this oil shows that it is mostly the methylol derivative of N-[N-methylaminocarbonyloxy]ethanimidothioic acid, methyl ester, namely N-[N-(hydroxymethyl)-N-(methyl)aminocarbonyloxy]-ethanimidothioic acid, methyl ester. In particular, the NMR (60 MHz) shows a singlet band at $\delta$ 3.0 (CDCl$_3$), corresponding to the N-methyl group, whereas the starting material shows a doublet for N-methyl. Also the NMR spectrum shows a singlet band at $\delta$ 4.8, corresponding to the methylene (CH$_2$) group of the methylol function; this band is absent in the starting material.

C.

A mixture of 162 parts of N-[N-methylaminocarbonyloxy]ethanimidothioic acid, methyl ester, 60 parts of paraformaldehyde, 15 parts of sodium bicarbonate and 500 parts of water is stirred at ambient temperature (about 25°) for about sixty hours. The reaction mixture is extracted four times with methylene chloride, about 67 parts each time, to remove unreacted starting material; these extracts are discarded. The aqueous reaction mixture is then extracted with 1350 parts of methylene chloride. The solvent is distilled from this extract, yielding an oil which slowly crystallizes on standing. The crude product is stirred with benzene, filtered and dried. After recrystallization from benzene, purified N-[N-(hydroxymethyl)-N-methylaminocarbonyloxy]ethanimidothioic acid, methyl ester, is obtained, m.p. 84°–85.5°.

Anal. calc'd for C$_6$H$_{12}$N$_2$O$_3$S: C, 37.48; H, 6.29; N, 14.58 S, 16.68 Found: C, 37.47, 37.78; H, 6.59 6.50; N, 14.67, 14.67; S, 16.31.

The following compounds of formula I can be reacted with formaldehyde. The physical properties (melting point or refractive index) shown in Table I refer to the monomethylol derivative of the compound of formula I, i.e. to the compound of formula III or formula V.

Table I $$R_1-C=NO-\overset{\overset{O}{\|}}{C}-\overset{\overset{H}{|}}{N}-R_3$$
$$|$$
$$S-R_2$$

| R$_1$ | R$_2$ | R$_3$ | Physical properties of the monomethylol derivative |
|---|---|---|---|
| CH$_3$ | CH$_3$ | H | m.p. 105°–106.5° |
| CH$_3$CH$_2$ | CH$_3$ | CH$_3$ | m.p. 83°–84° |
| CH$_3$\>CH<br>CH$_3$/ | CH$_3$ | CH$_3$ | N$_D^{25}$1.5137 |
| CH$_3$CH$_2$CH$_2$ | CH$_3$ | CH$_3$ | |
| CH$_3$ | CH$_3$CH$_2$ | CH$_3$ | |
| CH$_3$ | CH$_3$\>CH<br>CH$_3$/ | CH$_3$ | |
| CH$_3$CH$_2$ | CH$_3$CH$_2$CH$_2$ | CH$_3$ | |
| CH$_3$CH$_2$ | CH$_3$CH$_2$ | CH$_3$ | m.p. 78°–79° |

Use

The compositions of this invention are useful for control of insects which are detrimental to agriculture. For purposes of the present discussion of Use, the compositions include (a) the reaction product of formaldehyde and a compound of formula I, (b) unreacted compound of formula I, and (c) unreacted formaldehyde. No need is present to isolate components of the reaction, e.g., to remove formaldehyde, if present, prior to use.

As demonstrated in Examples 2 to 4 below, improved residual and insecticidal properties as well as decreased phytotoxicity are obtained of a formulation containing a compound of formula I, i.e., methomyl in these examples. The added use of a reaction product of such compound of formula I with formaldehyde is shown to give beneficial results. At least one of the compounds of formula II, namely of the formula

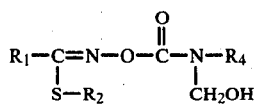

where
- $R_1$ is a branched or straight chain alkyl of 1–3 carbon atoms;
- $R_2$ is a branched or straight chain alkyl of 1–3 carbon atoms; and
- $R_4$ is methyl, hydrogen or $CH_2OH$ is present in the reaction product in a substantial amount and aids in providing insecticidal properties to the composition.

The compositions readily control pestiferous insects belonging to such orders as Lepidoptera, Coleoptera, Homoptera and Diptera. More specifically, insects controlled by the compounds of this invention include but are not limited to: cotton bollworm (*Heliothis zea*), tobacco budworm (*Heliothis virescens*), southern armyworm (*Spodoptera eridania*), beet armyworm (*Spodoptera exigua*), soybean looper (*Pseudoplusia includens*), Mexican bean beetle (*Epilachna varivestis*), green peach aphid (*Myzus persicae*) and the house fly (*Musca domestica*).

The insects are controlled by applying the composition in a convenient formulation (e.g. water) to the locus of infestation, to the area to be protected, or to the pests themselves. For the control of insects in agricultural crops, the composition is generally applied to the foliage or other plant parts which are infested or which are to be protected. Effective amounts to be applied depend upon the species to be controlled, its life stage, its size and location, the amount of rainfall, the time of year, moisture, temperature, type of application, and other variables. In general, 0.1 to 50 kg/ha may be required for insect control in agriculture with rates of 0.15 to 10 kg/ha usually being sufficient. Lower rates of 0.2 to 4 kg/ha may be used in many situations. In large-scale field operations rates in the range of ¼ to 2 kg/ha are generally used. It is understood that the rates disclosed are governed to a large extent by the concentration of the compounds present in the composition, e.g. whether unreacted formaldehyde (or unreacted formula I compound) is present in a greater concentration in comparison to a second composition. Higher concentration than those stated for application can also be used.

The compositions of this invention will generally be used in formulation with a carrier that commonly will consist of oil or water. Applications may be made with concentrated or dilute solutions or suspensions of the insecticide in the carrier. Low-volume applications utilizing dispersions containing about 20% of the active ingredient may be preferred by some applicators while others may prefer dilute solutions or suspensions containing only 80 ppm in high-volume applications.

The compositions of this invention possess significant advantages over prior art compounds, e.g. compositions containing a reaction product of methomyl and formaldehyde, unreacted methomyl and unreacted formaldehyde in comparison to a composition containing methomyl as its sole insecticidally active compound. Methomyl and methyl N-[N-(methylaminocarbonyloxy)e-thanimidothioic acid, methyl ester refer to the same compound in this disclosure and are used interchangeably. Fewer applications are required to provide a given level of insect control due to this distinctly longer residual insecticidal action. Use of fewer applications results in greater economy to the grower and dissemination of less insecticide in the environment. An additional advantage is lower phytotoxicity to cotton.

Conventionally, the compositions will be incorporated into a formulation in a known manner with incorporation of other components such as (a) surfactants, (b) diluents, (c) additives to reduce foam or corrosion, or (d) preservatives to control microbiological growth.

The compositions of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

Fungicides methyl 2-benzimidazolecarbamate
tetramethyl thiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
N-trichloromethylthiotetrahydrophthalimide (captan)
N-trichloromethylthiophthalimide (folpet)

Bactericides tribasic copper sulfate
streptomycin sulfate

Acaricides senecioic acid, ester with 2-sec-butyl-4,6-dinitrophenol ("Morocide")
6-methyl-1,3-dithiolo[2,3-B]quinonolin-2-one ("Morestan")
ethyl 4,4'-dichlorobenzilate (Chlorobenzilate ®)
1,1-bis(p-chlorophenyl)-2,2,2-trichloroethane
bis(pentachloro-2,4-cyclopentadien-1yl) (Pentac ®)
tricyclohexyl trihydroxide (Plictran ®)

Nematicides

S-methyl 1-(dimethylcarbamoyl)-N-(methylcarbamoyloxy)-thioformimidate
S-methyl 1-carbamoyl-N-(methylcarbamoyloxy)thioformimidate
N-isopropylphosphoramidic acid, O-ethyl-O'-[4-(methylthio)-m-tolyl]diester ("Nemacur")

Insecticides methylcarbamic acid, ester with 2,3-dihydro-2,2-dimethyl-7-benzofuranol (Furadan ®)

O-[2,4,5-trichloro-α-(chloromethyl)benzyl]phosphoric acid, O',O'-dimethyl ester (Gardona ®)

2-mercaptosuccinic acid, diethyl ester, S-ester with thionophosphoric acid, dimethyl ester (Malathion ®)

phosphorothioic acid, O,O-dimethyl, O-p-nitrophenyl ester (methyl parathion)

methylcarbamic acid, ester with α-naphthol (Sevin ®)

methyl O-(methylcarbamoyl)thiolacetohydroxamate (methomyl)

N'-(4-chloro-o-tolyl)-N,N-dimethylformamidine (Galecron ®)

O,O-diethyl-O-(2-isopropyl-4-methyl-6-pyrimidylphosphorothioate (Diazinon ®)

EXAMPLE 2

The foliage only of red kidney bean plants in the 2-leaf stage (8 days from planting) was sprayed to run-off with solutions of the composition of Example 1A at the dilutions indicated. The sprays contained a surfactant (Duponol L 144-WDG) at a concentration of 1:3000 by weight. Another set of plants were similarly treated with methomyl. After drying, leaves were excised and placed singly into covered 20×100 mm Petri dishes each containing 10 southern armyworm larvae, approximately 13 mm in length. Insect mortality was evaluated 2 days later and is recorded below.

| Treatment | Concentration % by Weight | % Mortality 2 Days |
|---|---|---|
| [1]Composition of Ex. 1A | 0.01 | 97 |
| | 0.005 | 77 |
| | 0.0025 | 7 |
| methomyl | 0.01 | 93 |
| | 0.005 | 40 |
| | 0.0025 | 30 |

[1]For composition of Ex. 1A, the concentration is calculated solely on the basis of methomyl used as starting material.

EXAMPLE 3

The foliage only of red kidney bean plants in the two-leaf stage (8 days after planting) was sprayed to run-off with solutions of the composition of Example 1A at the dilutions indicated. The sprays contained a surfactant Duponol L 144-WDG at 1:3000 (by weight). Another set of plants was similarly treated with methomyl. After drying plants were kept in a growth room maintained at 77°±2° F. and 53±5% relative humidity. One day after spraying and 6 days after spraying leaves were excised and placed singly into covered 20×100 mm Petri dishes each containing 10 southern armyworm larvae, approximately 13 mm in length. Insect mortality was evaluated 2 days later. Results are set forth below:

| Treatment | Concentration % by Weight | % Mortality 1-Day Residual | (2 Days) 6-Day Residual |
|---|---|---|---|
| [1]Composition of Ex. 1A | .04 | 100 | 95 |
| | .02 | 60 | 50 |
| | .01 | 15 | 15 |
| methomyl | .04 | 65 | 5 |
| | .02 | 10 | 0 |
| | .01 | 35 | 0 |

[1]For composition of Ex. 1A, the concentration is calculated solely on the basis of methomyl used as starting material.

EXAMPLE 4

Cotton plants approximately 25 cm in height having 4-5 true leaves were sprayed to run-off with solutions of the composition of Example 1A at the dilutions indicated. The sprays contained a surfactant (Duponol L 144-WDG) at a concentration of 1:3000 by weight. Another set of plants was similarly treated with methomyl. After drying plants were set out in the greenhouse and held for observation. After the first evaluation 5 days after spraying, plants received a second treatment at the same concentration of active ingredient and held an additional 7 days for final evaluation. Results are recorded below.

| Treatment | Concentration % by Weight (Each treatment | Phytotoxicity Ratings[2] at times indicated | |
|---|---|---|---|
| | | 5 days after first application | 12 days after first application and 7 days after second application |
| Composition of Ex. 1A | 0.05 | 0.25B | 3B |
| methomyl | 0.05 | 2.5B | 5B |

[2]Rating on the basis of 0-10 with 10 being completely dead. "B" indicates burn.

What is claimed is:

1. A composition comprising a reaction product of formaldehyde and a compound of the formula

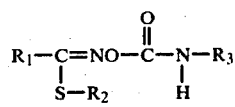

where
$R_1$ is branched or straight chain alkyl of 1-3 carbon atoms;
$R_2$ is branched or straight chain alkyl of 1-3 carbon atoms; and
$R_3$ is hydrogen or methyl;
whereby the reaction product is formed by contacting said compound with formaldehyde at a molar ratio in a range of 1:0.1 to 1:50.

2. The composition of claim 1 where said compound is N-[N-(methyl)aminocarbonyloxy]ethanimidothioic acid, methyl ester.

3. The composition of claim 1 which contains unreacted compound.

4. The composition of claim 3 which contains formaldehyde which is unreacted.

5. The composition of claim 4 wherein siad compound is N-[N-(hydroxymethyl)-N-methylaminocarbonyl]ethanimidothioic acid, methyl ester.

6. The composition of claim 3 where said compound is N-[N-(methyl)aminocarbonyloxy]ethanimidothioic acid, methyl ester.

7. The composition of claim 3 where said molar ratio is in a range from 1:0.5 to 1:5.

8. The composition of claim 7 where said compound is N-[N-(methyl)aminocarbonyloxy]ethanimidothioic acid, methyl ester.

9. The compound of claim 7 where said molar ratio is in a range from 1:1 to 1:3.

10. The composition of claim 9 wherein said compound is N-[N-(methyl)aminocarbonyloxy]ethanimidothioic acid, methyl ester.

11. A method for control of insects comprising applying to a locus to be protected an insecticidally effective amount of a composition of claim 1.

12. A method for control of insects comprising applying to a locus to be protected an insecticidally effective amount of a composition of claim 2.

13. A method for control of insects comprising applying to a locus to be protected an insecticidally effective amount of a composition of claim 3.

14. A method for control of insects comprising applying to a locus to be protected an insecticidally effective amount of a composition of claim 4.

15. A method for control of insects comprising applying to a locus to be protected an insecticidally effective amount of a composition of claim 5.

16. A method for control of insects comprising applying to a locus to be protected an insecticidally effective amount of a composition of claim 6.

17. A method for control of insects comprising applying to a locus to be protected an insecticidally effective amount of a composition of claim 7.

18. A method for control of insects comprising applying to a locus to be protected an insecticidally effective amount of a composition of claim 8.

19. A method for control of insects comprising applying to a locus to be protected an insecticidally effective amount of a composition of claim 9.

20. A method for control of insects comprising applying to a locus to be protected an insecticidally effective amount of a composition of claim 10.

21. A compound of the formula

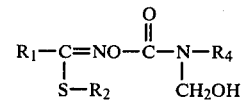

where
$R_1$ is branched or straight chain alkyl of 1-3 carbon atoms;
$R_2$ is branched or straight chain alkyl of 1-3 carbon atoms; and
$R_4$ is hydrogen, methyl or $CH_2OH$.

22. A compound of claim 21 where
$R_1$ is methyl or ethyl;
$R_2$ is methyl or ethyl; and
$R_4$ is hydrogen or methyl.

23. The compound of claim 21 which is N-[N-(hydroxymethyl)-N-methylaminocarbonyloxy]ethanimidothioic acid, methyl ester.

24. The compound of claim 21 which is N-[N-(hydroxymethyl)aminocarbonyloxy]ethanimidothioic acid, methyl ester.

25. The composition of claim 1 whereby a temperature of between about 0° C. and 100° C. is employed in contacting said compound and formaldehyde.

26. The composition of claim 25 where said temperature is between 20° C. and 60° C.

* * * * *